US010364944B2

(12) United States Patent
Van Bommel et al.

(10) Patent No.: US 10,364,944 B2
(45) Date of Patent: Jul. 30, 2019

(54) VISIBLE AND UV LIGHTING SYSTEM

(71) Applicant: SIGNIFY HOLDING B.V., Eindhoven (NL)

(72) Inventors: Ties Van Bommel, Horst (NL); Rifat Ata Mustafa Hikmet, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 15/832,350

(22) Filed: Dec. 5, 2017

(65) Prior Publication Data
US 2018/0172219 A1 Jun. 21, 2018

(30) Foreign Application Priority Data

Dec. 15, 2016 (EP) .................................. 16204420

(51) Int. Cl.
F21K 9/237 (2016.01)
F21V 7/00 (2006.01)
A61N 5/06 (2006.01)
F21V 3/04 (2018.01)
F21V 7/06 (2006.01)
F21V 7/22 (2018.01)
(Continued)

(52) U.S. Cl.
CPC ............ *F21K 9/237* (2016.08); *A61N 5/0614* (2013.01); *A61N 5/0616* (2013.01); *A61N 5/0624* (2013.01); *F21V 3/049* (2013.01); *F21V 7/0016* (2013.01); *F21V 7/06* (2013.01); *A61N 2005/0615* (2013.01); *A61N 2005/0661* (2013.01); *A61N 2005/0663* (2013.01); *A61N 2005/0666* (2013.01); *F21K 9/62* (2016.08); *F21V 7/0008* (2013.01); *F21V 7/22* (2013.01); *F21Y 2113/13* (2016.08); *F21Y 2115/10* (2016.08)

(58) Field of Classification Search
CPC ... F21K 9/237; F21K 9/62; F21V 7/06; F21V 3/049; F21V 7/0016; F21V 7/0008; F21V 7/22; A61N 5/06; A61N 2005/0615; A61N 5/0616; A61N 5/0624; A61N 5/0614; A61N 2005/0663; A61N 2005/0666; A61N 2005/0661; F21Y 2115/10; F21Y 2113/13
See application file for complete search history.

(56) References Cited

U.S. PATENT DOCUMENTS 8,262,251 B2   9/2012 Rains, Jr. et al.
9,347,622 B2   5/2016 Ulasyuk et al.
(Continued)

FOREIGN PATENT DOCUMENTS

EP   2177820 A2    4/2010
WO   2008052318 A1  5/2008
(Continued)

OTHER PUBLICATIONS

European Search Report Application No. EP 17205356 (Year: 2018).*

*Primary Examiner* — Anh T Mai
*Assistant Examiner* — Glenn D Zimmerman

(57) ABSTRACT

A lighting system combines an arrangement of UV LEDs which face a light exit window and an arrangement of visible light LEDs which face a reflector arrangement. The reflection can be used to provide desired beam shaping or diffusion so that beam shaping components are not needed at the exit window. In this way, UV deterioration of beam shaping components is avoided.

14 Claims, 6 Drawing Sheets

(51) Int. Cl.
  *F21K 9/62* (2016.01)
  *F21Y 115/10* (2016.01)
  *F21Y 113/13* (2016.01)

(56) References Cited

U.S. PATENT DOCUMENTS

| | | |
|---|---|---|
| 2005/0219476 A1 | 10/2005 | Beeson et al. |
| 2006/0271024 A1* | 11/2006 | Gertner ............... A61N 5/0603 606/2 |
| 2007/0045524 A1 | 3/2007 | Rains, Jr. et al. |
| 2008/0205053 A1* | 8/2008 | Rains ....................... F21S 2/00 362/231 |
| 2010/0327745 A1 | 12/2010 | Dassanayakke et al. |
| 2012/0199005 A1 | 8/2012 | Koji et al. |
| 2013/0141908 A1* | 6/2013 | Rodriguez .............. F21V 5/007 362/240 |
| 2016/0020371 A1* | 1/2016 | Kang ..................... H01L 33/60 257/91 |

FOREIGN PATENT DOCUMENTS

| | | |
|---|---|---|
| WO | 2008135927 A1 | 11/2008 |
| WO | 2015168783 A1 | 11/2015 |
| WO | 2016202736 A1 | 12/2016 |
| WO | 2017125322 A1 | 7/2017 |

\* cited by examiner

A

B

C

US 10,364,944 B2

VISIBLE AND UV LIGHTING SYSTEM

FIELD OF THE INVENTION

This invention relates to lighting systems, in particular for providing visible light as well as UV light, which enables the synthesis in the human body of vitamin D.

BACKGROUND OF THE INVENTION

People spend approximately 90% of their time indoors, a substantial amount of this at work, in an office.

White light sources can produce high quality light with a color rendering index above 90 with very high efficiencies. In general, compared with natural sunlight, such light sources do not have certain parts of the spectrum, such as the UV part of the electromagnetic spectrum.

However, natural sunlight, and the UV content in particular, is essential for the human body, for example for vitamin D production. It would therefore be desirable to have times during the working day when exposed to natural sunlight. This exposure for example would help the prevention of osteomalacia in adults. Studies have found that 90% of the population worldwide is below sufficient levels of Vitamin D, because of too limited exposure to sunlight, and in particular the UV component of natural sunlight, especially in winter time. A correlation between low vitamin D levels and the incidence of a large number of health issues has been identified, for example mood, energy, muscle weakness, cardiovascular disease, multiple sclerosis, diabetes, obesity, depression, Alzheimer's, cancers, etc.

More and more people want a better work-life balance, and would therefore appreciate exposure to more healthy lighting during the working day. In addition, increasing numbers of people take vitamin D supplements for the prevention of osteomalacia, because of the problem that artificial lighting does not enable sufficient synthesis of vitamin D.

However, it is not easy to provide natural sunlight in an office environment. There is therefore a need for a lighting system which is able to replicate the benefits of natural sunlight, but which can be used in an indoor environment, such as an office environment.

For this purpose, it is possible to introduce UV LEDs in combination with white LEDs and also colored light. Furthermore, the use of UV LEDs has also been proposed for producing both white light and also colored light.

Low intensity UV light may also be used for other applications such as for skin tanning, insect attraction, skin treatment, disinfection, etc. Thus, systems which provide UV light as well as visible light have applications other than for emulating natural daylight.

It is known that UV light tends to degrade many of the polymers which are used in current lighting applications, for example in a lighting diffuser.

There is therefore a need for a lighting system which enables the provision of UV lighting as well as visible lighting, but without degrading the polymers which are desired in the lighting system.

SUMMARY OF THE INVENTION

The invention is defined by the claims.

According to examples in accordance with an aspect of the invention, there is provided a lighting system, comprising:

a housing which comprises a support structure and a light exit window for emitting light to the ambient surroundings of the lighting system;

an arrangement of UV LEDs mounted on the support structure, wherein the UV LEDs face the light exit window;

an arrangement of visible light LEDs mounted on the support structure; and a reflector arrangement, wherein the visible light LEDs face the reflector arrangement, and the reflector arrangement is for reflecting the visible light output from the visible light LEDs to the exit window.

Note that the term "light" is used broadly to refer to the full electromagnetic spectrum, i.e. visible and UV light. The term "light exit window" should for example be understood accordingly.

This system provides the output of UV LEDs directly to a light exit window of the lighting system, whereas visible light LEDs deliver their output after reflection. This reflection can thus be used to provide desired beam shaping or diffusion so that beam shaping components are not needed at the exit window. In this way, UV deterioration of beam shaping components is avoided. The reflector arrangement defines a light mixing chamber particularly if diffuse reflections are provided or it defines a more controlled a reflection profile particularly if specular reflections are provided.

By way of example, no diffuser is used at the light exit window, as would normally be used in order to hide spottiness. Instead, the output of the visible light LEDs is indirectly reflected to the outside.

The system may further comprise a UV beam shaping arrangement for shaping the output of the UV LEDs. This is used to ensure that all, or nearly all of the UV LED output passes to the light exit window and thus does not cause deterioration of other components. The UV light is prevented from reaching the UV sensitive parts of the light arrangement such as the visible light LEDs or the polymer materials of the reflector arrangement.

The UV LEDs thus provide direct lighting. The beam shaping arrangement is insensitive to UV light, and may for example comprise a metallic shroud around each UV LED or around sets of UV LEDs.

Alternatively, the beam shaping arrangement may comprise a shaped part of the support structure. This provides a more integrated design with fewer components.

The beam shaping arrangement is for example adapted to direct at least 80% of the output of the UV LEDs directly to the exit window, for example at least 85%, for example at least 90%.

At most 20% of the visible light output from the visible light LEDs may directly reach the light exit window, for example at most 15%, for example at most 10%.

Thus, some direct light output from the visible light LEDs can be allowed, with the reflected light still providing the desired shielding of the visible appearance of the LEDs. Similarly, a small proportion (i.e. intensity) of the UV output may not directly reach the light exit window, as long as that proportion has a sufficiently low intensity to avoid damage to the materials on which that UV output is incident.

The system may however be designed so that there is no direct path from the visible light LEDs to the light exit window and so that all UV output is directed to the light exit window.

The housing for example defines a mixing chamber, with the UV LEDs at a top part and the light exit window at a bottom part. The UV LEDs then simply deliver a downward UV output through the light exit window.

The visible light LEDs preferably face into the mixing chamber.

In one example, the visible light LEDs are mounted on a rim around the light exit window facing the top part, directly or at an angle. Thus, they face generally upwardly if the system is mounted with the light exit window facing downwardly.

In another example, the mixing chamber comprises one or more side wall portions and a top wall portion which forms the top part, wherein the visible light LEDs are mounted on the one or more side wall portions facing across the mixing chamber. Thus, the visible light LEDs face sideways.

In another example, the visible light LEDs are at the top part facing in the direction of the light exit window, and the reflector arrangement comprises reflector portions over the visible light LEDs to block the light path to the light exit window. In this case, all of the LEDs can be mounted on the same surface facing the same (i.e. parallel) direction. The direct light path from the visible LEDs is however blocked by reflector portions. This may be easier to manufacture.

The light exit window may comprise an empty opening formed in the housing. Thus, the UV output does not pass through any intermediate components at all.

Alternatively, the light exit window may have a solid transparent UV-resistant closure. This can protect the internal components of the lighting system.

The UV LEDs for example comprise UV-B LEDs and the visible light LEDs for example comprise LEDs for delivering white light, such as white LEDs or RGB LED arrangements controllable to deliver a white light output.

The lighting system may comprise an LED lamp (reflector lamp or tubular lamp) or an LED luminaire.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a lighting system which combines an arrangement of UV LEDs which face a light exit window and an arrangement of visible light LEDs which face a reflector arrangement. The reflection can be used to provide desired beam shaping or diffusion so that beam shaping components are not needed at the exit window. In this way, UV deterioration of beam shaping components is avoided.

Figure 1:
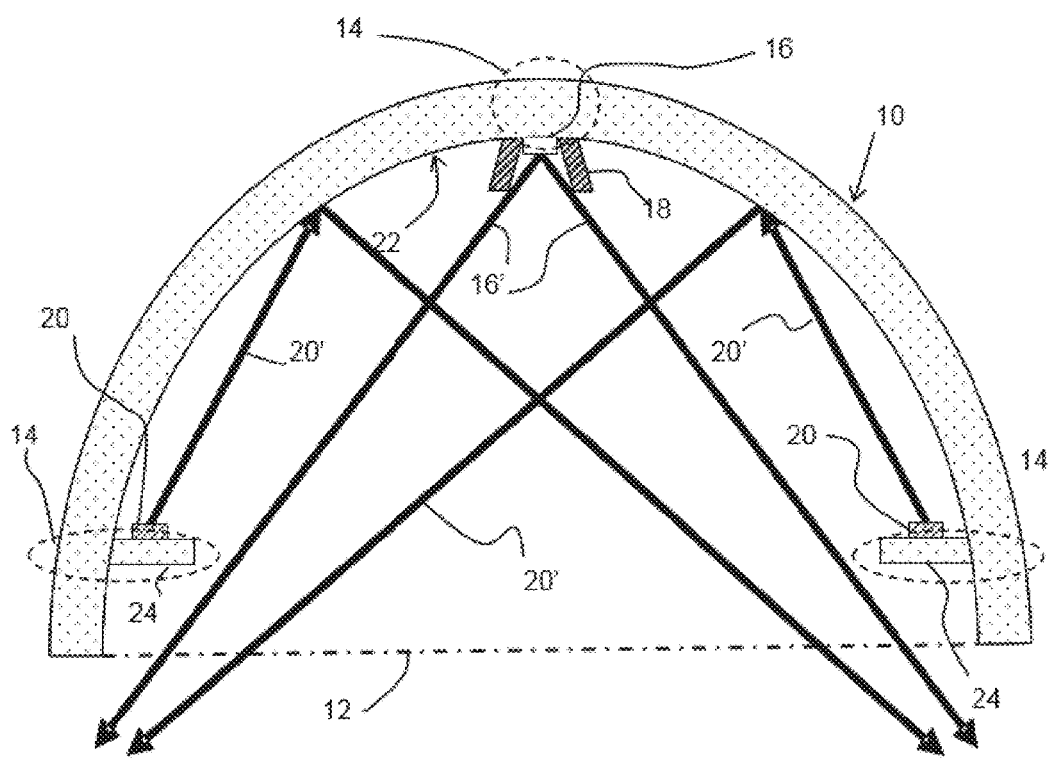
FIG. 1 shows a lighting system for providing visible and UV light.

FIG. 1 shows a lighting system for providing visible and UV light into an area to be illuminated.

The system comprises a housing 10 which comprises a support structure on which LEDs can be mounted and a light exit window 12. The support structure in this example is an integral part of the housing, and comprises regions 14 of the housing.

An arrangement of one or more UV LEDs 16 is mounted on the support structure in particular at a top part of the housing 10. The light exit window 12 is at a bottom part of the housing. The UV LEDs deliver a downward UV output through the light exit window. The UV LEDs emit light with a wavelength from 100 nm to 400 nm.

FIG. 1 shows a single UV LED, but there may be an array of two or more UV LEDs. The UV LEDs face the light exit window 12 so that their output 16' is mainly directed to the exit window 12 without interacting with other parts of the system.

By way of example, at least 80% of the output 16' of the UV LEDs (as a fraction of the total light intensity) is directed to the exit window. There may be at least 85%, or at least 90% of the UV LED output directed to the exit window 12. Thus, some of the UV output may not directly reach the light exit window.

The UV LED may be in the form of a package which has an output beam shape which achieves this directional control, without needing further beam shaping optics. However, FIG. 1 shows a beam shaping shroud 18 around the UV LED 16 for limiting the angular spread of the output UV light to confine its direction generally towards the exit window 12. The beam shaping shroud is insensitive to UV light. The beam shaper may be a metallic reflector. Aluminum is a preferred reflector material as it has good reflectivity of UV. It may also be a multi-layer reflector.

An arrangement of visible light LEDs 20 is also mounted on the support structure 14. The visible light LEDs emit light in a wavelength from 400 nm to 800 nm. The visible light LEDs do not face the light exit window but instead face into the housing. The housing functions as a mixing chamber and for this purpose it has a reflective inner surface 22 which functions as a reflector arrangement. The reflector arrangement is thus in this example an integral part of the main outer housing, but a separate housing and reflector may instead be provided.

The visible light LEDs 20 face the reflector arrangement, i.e. the inner surface 22. The reflector arrangement reflects the visible light output 20' from the visible light LEDs to the exit window. There may be a single or multiple reflections before the light eventually reaches the exit window 12. The effect is to provide light mixing and/or redirection, thereby preventing the LEDs being visible.

Some light from the visible light LEDs may directly reach the light exit window 12, but the majority undergoes one or more reflections first. The reflection may be specular or diffuse depending on the desired output beam characteristics. By way of example, at most 20% of the visible light output from the visible light LEDs may directly reach the light exit window, for example at most 15%, for example at most 10%.

Thus, some direct light output from the visible light LEDs can be allowed.

The design of the reflector arrangement, in combination with the output characteristics of the visible light LEDs 20, is chosen to achieve a desired beam direction, beam spread and degree of collimation for the visible light for the desired lighting application.

In the example shown in FIG. 1, the visible light LEDs 20 are provided on a rim 24 around the light exit window. The visible light LEDs 20 are mounted on the rim facing upwardly (i.e. facing the top part of the housing). The rim 24 may be set back from the opening as shown, or it may be coplanar with the light exit opening 12, and thus define the light exit opening (as in the examples shown in FIGS. 2 and 3).

This system provides most or all of the output of the UV LEDs 16 directly to the light exit window whereas the visible light LEDs 20 deliver their output after reflection. UV deterioration of components is avoided.

The light exit window 12 may be an opening, so that no components are in the path of the UV light. For example, no diffuser is used at the light exit window.

FIG. 1 shows the housing having a generally an arcuate (circular or elliptical) cross sectional shape. The lighting system may be rotationally symmetric and hence have a housing which is generally part-spherical or part-ellipsoidal. Alternatively, the lighting system may be elongate with a constant cross sectional shape, hence forming a generally cylindrical design.

As explained above, the particular shape is designed with the desired light output taken into consideration.

FIG. 2 shows various modifications to the design of FIG. 1. It shows an angular housing design with a top portion 30 and side portions 32 and a lower rim 24 which defines the light exit opening 12.

Figure 2A:
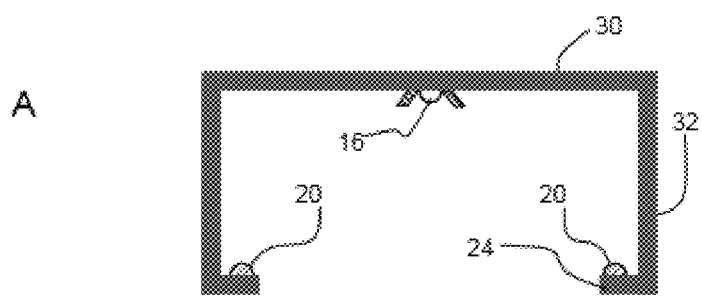
FIGS. 2A-2D show various modifications to the design of FIG. 1.

FIG. 2A shows generally same arrangement as FIG. 1 but with the angular design and the rim 24 defining the exit window. There are two visible light LEDs shown. There may however be a ring of LEDs around the light exit window, for example on an annular circuit board which sits on the rim 24. This would then provide a more rotationally symmetric and smooth light output pattern.

Figure 2B:
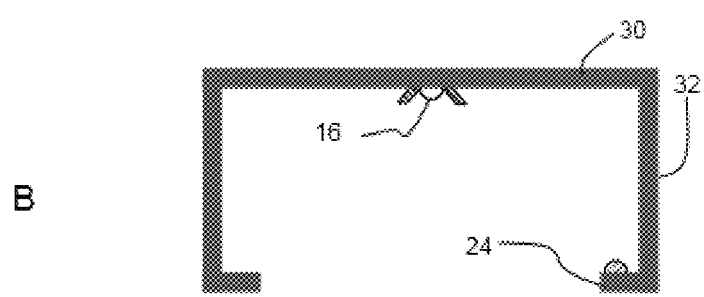

FIG. 2B shows that there may be only a single visible light LED 20.

Figure 2C:
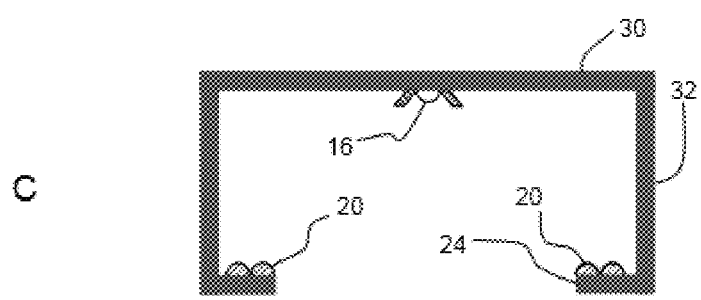

FIG. 2C shows that there may be multiple visible light LEDs at each side of the light exit window. They may then form multiple concentric rings around the light exit window, again for example on an annular circuit board which sits on the rim 24. For a cylindrical design, there are then multiple lines of visible LEDs along the length of the system.

Figure 2D:
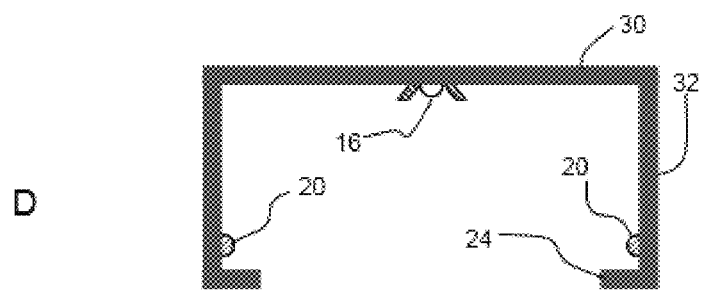

FIG. 2D shows that the visible light LEDs 20 may be provided on the side wall portions 32, so that they face across the mixing chamber. Thus, the visible light LEDs face sideways.

FIG. 3 shows further designs.

Figure 3A:
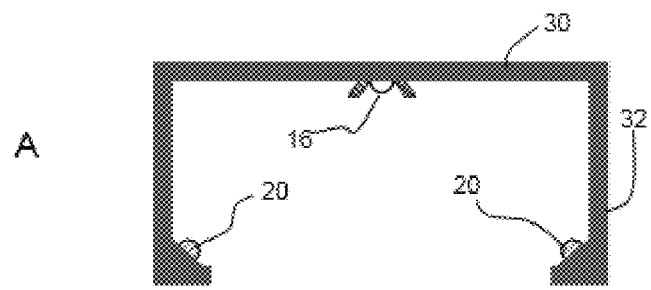
FIGS. 3A-3D show further modifications to the designs of FIG. 1.

FIG. 3A shows that the visible light LEDs 20 do not need to face directly upwardly. They may be directed at an angle to the upright direction to provide light diagonally across the mixing chamber.

Figure 3B:
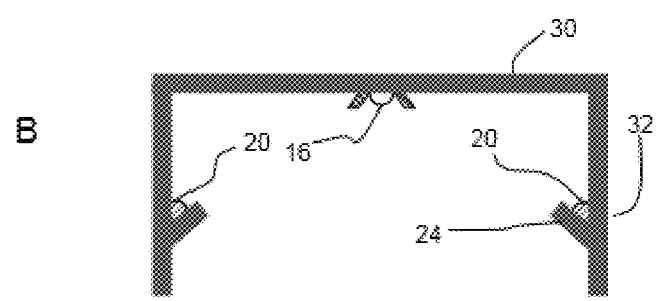

FIG. 3B shows that the rim 24 on which the visible light LEDs 20 are mounted may also perform a beam shaping function. The reflecting surface can be angled to limit the spread of light output.

Figure 3C:
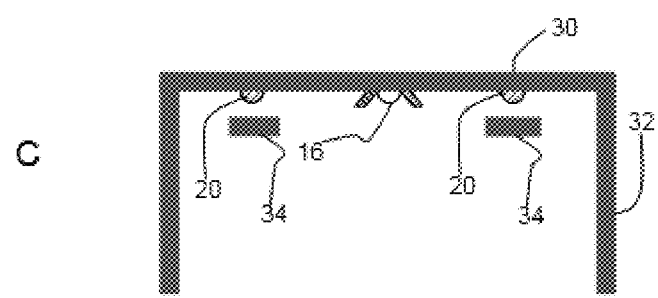

FIG. 3C shows that the reflector arrangement may include features other than the outer housing. The visible light LEDs are mounted at the top part 30 facing in the direction of the light exit window. However, the reflector arrangement comprises reflector portions 34 over the visible light LEDs to block the light path to the light exit window. All of the LEDs 16, 20 can then be mounted on the same surface which can ease manufacture. FIG. 3 also shows that the light exit opening may then cover the full area of the bottom of the housing, without any rim.

Figure 3D:
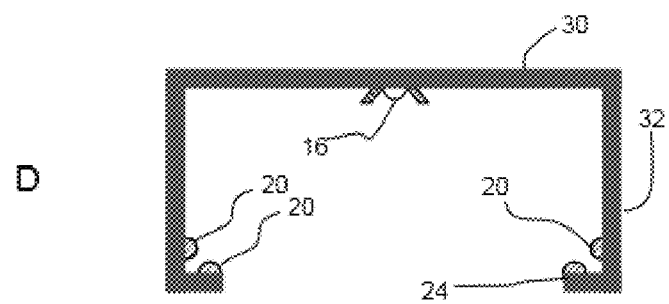

FIG. 3D shows that the visible light LEDs 20 may face in different directions, by combining different configurations as described above. In FIG. 3D there are visible light LEDs facing upwardly as well as inwardly across the light mixing chamber.

FIG. 4 shows further designs.

Figure 4A:
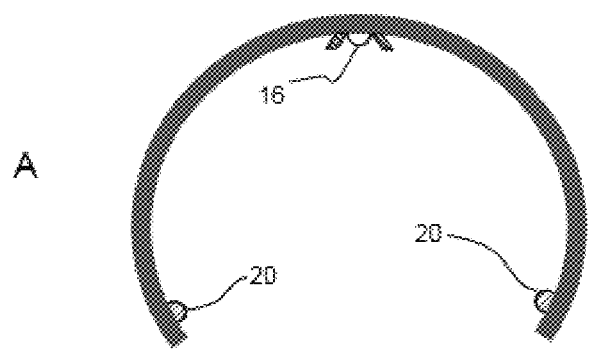
FIGS. 4A-4C show further modifications to the designs of FIG. 1.

FIG. 4A shows that the visible light LEDs may be mounted directly on side wall portions (of a curved reflector design in the example shown) instead of requiring an additional rim.

Figure 4B:
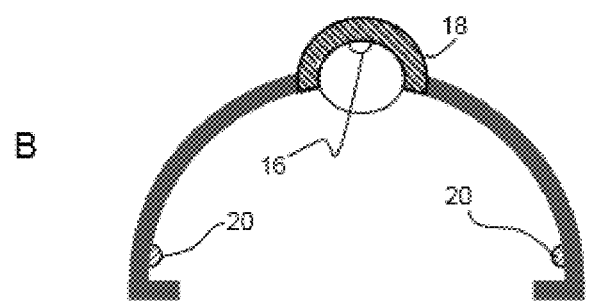

FIG. 4B shows that the beam shaping arrangement 18 of the UV LED 16 may comprise a shaped part of the support structure, i.e. the housing. This provides a more integrated design with fewer components. The housing may have the same material design throughout or they may be different reflection properties at the beam shaping arrangement 18.

Figure 4C:
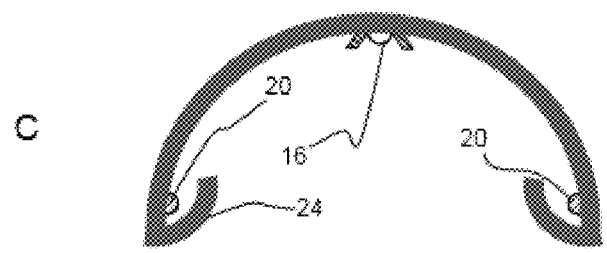

FIG. 4C shows that the design of the rim may provide a more complicated beam shaping function for the light output of the visible light LEDs 20.

FIG. 5 shows further designs.

Figure 5A:
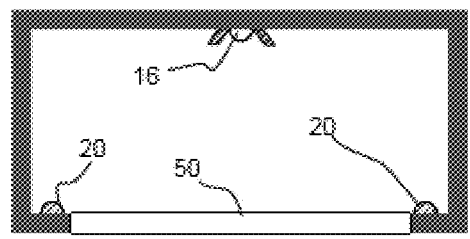
FIGS. 5A-5Cc show further modifications to the designs of FIG. 1.

As explained above, the light exit window 12 may be an empty opening in the housing. FIG. 5A shows that there may instead be a solid transparent UV-resistant closure 50. This does not need to be a diffuser and may instead be a transparent (to UV and to visible light) window, for example of glass or quartz or any other transparent substrate which is insensitive to UV.

Figure 5B:
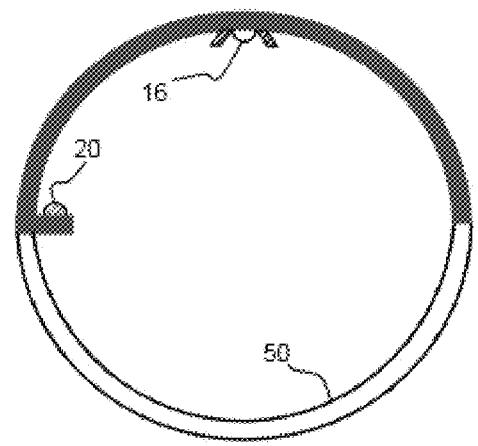

FIG. 5B shows that the closure 50 may be curved to form a cylindrical or spherical or ellipsoidal outer shape.

Figure 5C:
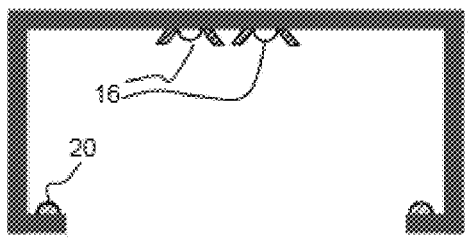

FIG. 5C shows that there may be multiple UV LEDs 16. This applies to all designs.

FIG. 6 shows further designs.

Figure 6A:
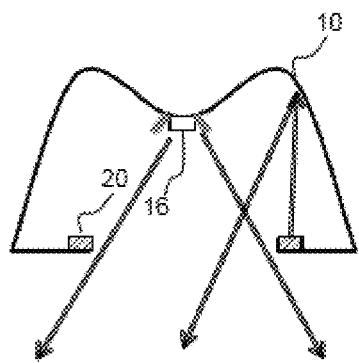
FIGS. 6A-6B show further modifications to the designs of FIG. 1.

FIG. 6A shows that a more complicated housing shape may be used. This example shows that the housing may define a specular reflecting surface which performs a collimation function. The specular reflective collimator may be designed such that it collimates the visible (e.g. white) light to form collimated indirect visible (e.g. white) light.

Figure 6B:
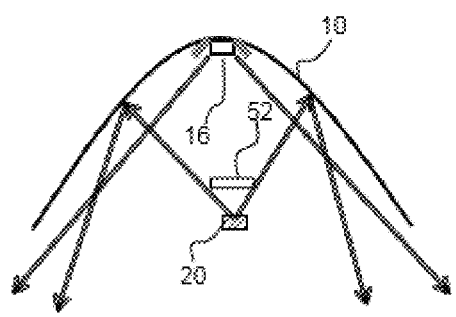

FIG. 6B shows a design with the visible light LED in the direct path of the UV LED 16 but protected by a shield 52 which may be an absorber or a reflector.

The UV LEDs for example comprise UV-B LEDs and the visible light LEDs for example comprise white light LEDs.

The housing, which forms the reflector arrangement and/or defines the mixing chamber, is preferably made from a plastic material, with a coating if required.

The plastic may be a silicone material, PMMA, PET, PC, PE. The plastic may be provided with reflective particles such as aluminum, silver flakes, $Al_2O_3$, $BaSO_4$, $TiO_2$, or combinations thereof. Alternatively, a reflective layer may be provided, such as aluminum or silver evaporated or deposited onto the plastic surface, or a polymer coating of reflective particles. The polymer coating may then comprise aluminum, silver flakes, $Al_2O_3$, $BaSO_4$, $TiO_2$, or combinations thereof in a matrix material such as polyvinyl butyral (PVB).

The reflectivity of the mixing chamber is for example higher than 80%, more preferably higher than 85%, most preferably above 90%.

The visible light LEDs are typically white light LEDs. The white light for example has a maximum deviation to the black body locus (BBL) of 15 standard deviations of color matching (SDCM), for example less than 10 SDCM or even 5 SDCM.

Preferably, the white light may have a color temperature in the range from 2,000 K to 8,000 K, for example 2,500 K to 6,000 K, for example 2,800 K to 5,000 K.

Preferably, the white light is light which has a color rendering index of at least 70, more preferably at least 80, and most preferably at least 85.

The UV LEDs are for example UV-B LEDs. They are designed to provide a dose of UV-B light which is sufficient to provide the advantages of vitamin D production, but not sufficient to cause skin damage. By way of example, the light intensity of the system as a whole is based on each UV-B LED having an output power of 400 μW to 800 μW. A total number of UV-B LEDs can be for example in the range 1 to 40, giving a total output power in the range 0.4 mW to 30 mW.

UV-B LEDs are commercially available, and are mainly used in medical applications, for example for medical photometry. There are also commercially available UV-B lighting products for stimulating plant growth for illuminating terrariums. The UV-B wavelength is in the range 280 nm to 315 nm.

The invention is not however limited to UV-B output, and the UV LEDs may operate in the UV-A or UV-C bands as well as, or instead of the UV-B band.

The invention is also not limited to white visible light. The invention may be applied to a system delivering any color output or indeed having a controllable color point and/or color temperature.

Figure 7:
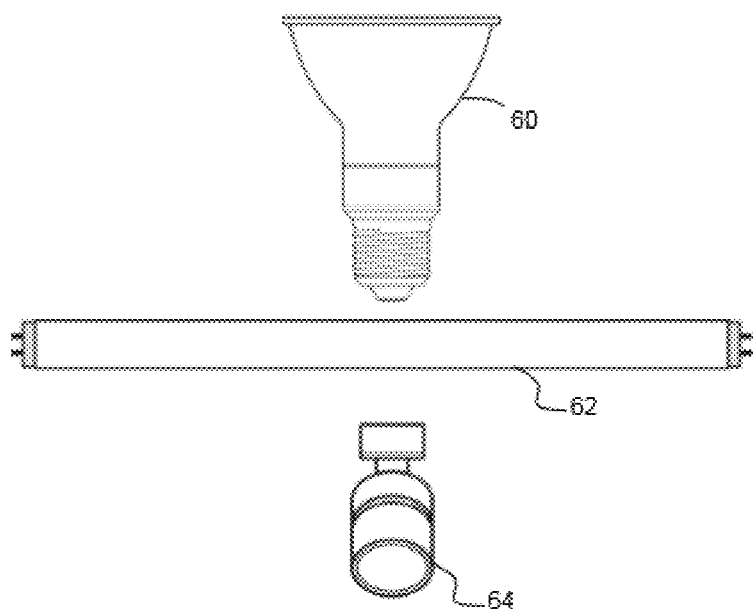
FIG. 7 shows lighting devices which may use the system.

FIG. 7 shows lighting devices which may use the system. The lighting system may comprise an LED lamp such as a reflector lamp 60 or a tubular LED lamp 62 or it may comprise an LED luminaire 64.

As mentioned above, the combined visible and UV lighting may be used to emulate natural daylight. Instead, the UV component may be for other purposes such as for skin tanning, insect attraction, skin treatment, disinfection, etc.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A lighting system, comprising:
   a housing which comprises a support structure and a light exit window for emitting light to the ambient surroundings of the lighting system;
   an arrangement of UV LEDs mounted on the support structure, wherein the UV LEDs directly face the light exit window;
   an arrangement of visible light LEDs mounted on the support structure;
   a reflector arrangement, wherein the visible light LEDs face the reflector arrangement, and the reflector arrangement is for reflecting the visible light output from the visible light LEDs to the exit window; and,
   a UV beam shaping arrangement for shaping the output of the UV LEDs such that nearly all of the output of the UV LEDs passes to the light exit window without reaching any of the visible light LEDs.

2. The lighting system as claimed in claim 1, wherein the UV beam shaping arrangement comprises a shaped part of the support structure.

3. The lighting system as claimed in claim 1, wherein the UV beam shaping arrangement comprises a respective metallic shroud around each UV LED or around sets of UV LEDs.

4. The lighting system as claimed in claim 1, wherein the UV beam shaping arrangement is adapted to direct at least 90% of the output of the UV LEDs directly to the exit window.

5. The lighting system as claimed in claim 1, wherein at most 10% of the visible light output from the visible light LEDs directly reaches the light exit window.

6. The lighting system as claimed in claim 1, wherein the housing defines a mixing chamber, with the UV LEDs at a top part and the light exit window at a bottom part.

7. The lighting system as claimed in claim 1, wherein the light exit window comprises an empty opening formed in the housing.

8. The lighting system as claimed in claim 1, wherein the light exit window has a solid transparent UV-resistant closure.

9. The lighting system as claimed in claim 1, wherein the UV LEDs comprise UV-B LEDs and the visible light LEDs comprise white light LEDs or LED arrangements capable of delivering a white light output.

10. The lighting system as claimed in claim 1, comprising an LED lamp selected from the group consisting of an LED reflector lamp, a tubular LED lamp, and an LED luminaire.

11. The lighting system as claimed in claim 6, wherein the visible light LEDs face into the mixing chamber.

12. The lighting system as claimed in claim 6, wherein the mixing chamber comprises one or more side wall portions and a top wall portion which forms the top part, wherein the visible light LEDs are mounted on the one or more side wall portions facing across the mixing chamber.

13. The lighting system as claimed in claim 6, wherein the visible light LEDs are at the top part facing in the direction of the light exit window, and the reflector arrangement comprises reflector portions over the visible light LEDs to block the light path to the light exit window.

14. The lighting system as claimed in claim 11, wherein the visible light LEDs are mounted on a rim around the light exit window facing the top part, directly or at an angle.

* * * * *